United States Patent
Hafiz et al.

(10) Patent No.: US 9,498,142 B2
(45) Date of Patent: Nov. 22, 2016

(54) MULTI-LAYERED STRUCTURE AND METHOD

(71) Applicant: Heraeus Precious Metals GmbH & Co. KG, Hanau (DE)

(72) Inventors: Jami A. Hafiz, Cedar Park, TX (US); Stefan Schibli, Frankfurt am Main (DE);

(Continued)

(73) Assignee: Heraeus Deutschland GmbH & Co. KG, Hanau (DE)

(*) Notice: Subject to any disclaimer, the term of this patent is extended or adjusted under 35 U.S.C. 154(b) by 22 days.

(21) Appl. No.: 14/323,163

(22) Filed: Jul. 3, 2014

(65) Prior Publication Data

US 2016/0005509 A1   Jan. 7, 2016

(51) Int. Cl.
*A61N 1/05* (2006.01)
*A61B 5/04* (2006.01)
(Continued)

(52) U.S. Cl.
CPC .............. *A61B 5/04* (2013.01); *A61B 5/6846* (2013.01); *A61B 5/6851* (2013.01); *A61N 1/05* (2013.01);
(Continued)

(58) Field of Classification Search
CPC .............. A61B 5/04; A61B 5/6846; A61B 5/6851; A61B 2562/125; H01B 1/127;
(Continued)

(56) References Cited

U.S. PATENT DOCUMENTS 3,994,302 A * 11/1976 Brennen .............. A61N 1/0452
607/115
6,034,295 A * 3/2000 Rehberg ................. A61B 17/72
433/201.1
(Continued)

FOREIGN PATENT DOCUMENTS

EP  2068146  6/2009
EP  2075274  7/2009
(Continued)

OTHER PUBLICATIONS

Office Action for U.S. Appl. No. 14/056,450 mailed May 11, 2015 (13 pages).
(Continued)

*Primary Examiner* — Michelle Mandala
*Assistant Examiner* — Thai T Vuong
(74) *Attorney, Agent, or Firm* — Dicke, Billig & Czaja, PLLC

(57) ABSTRACT

One aspect relates to a method for producing a layered structure, including providing a substrate, forming a first layer onto at least part of the substrate, the first layer being a first polymer, and forming a second layer onto at least part of the first layer, the second layer being a second polymer. The substrate and the second layer are electrically conductive and the first layer is insulating or the substrate and the second layer are insulating and the first layer is electrically conductive. Forming each of the first and second layers includes forming such that each layer is no more than one tenth of the thickness of the substrate.

13 Claims, 8 Drawing Sheets

(72) Inventors: Jens Troetzschel, Ronneburg-Neuwiedermus (DE)

(51) Int. Cl.
| | |
|---|---|
| *H01B 7/04* | (2006.01) |
| *H01B 1/12* | (2006.01) |
| *H01B 3/30* | (2006.01) |
| *A61B 5/00* | (2006.01) |
| *B21F 19/00* | (2006.01) |
| *H01L 51/00* | (2006.01) |
| *A61M 25/09* | (2006.01) |

(52) U.S. Cl.
CPC ............... *B21F 19/00* (2013.01); *H01B 1/127* (2013.01); *H01B 1/128* (2013.01); *H01B 3/307* (2013.01); *H01B 7/048* (2013.01); *A61B 2562/125* (2013.01); *A61M 2025/09108* (2013.01); *C08G 2261/1424* (2013.01); *C08G 2261/3223* (2013.01); *C08G 2261/51* (2013.01); *C08G 2261/65* (2013.01); *C08G 2261/70* (2013.01); *C08G 2261/79* (2013.01); *C08G 2261/90* (2013.01); *H01L 51/0037* (2013.01)

(58) Field of Classification Search
CPC ............ H01B 13/30; H01B 3/307; H01B 1/128; H01B 7/048; B21F 19/00; A61N 1/05; C08G 2261/51; C08G 2261/79; C08G 2261/70; H01L 51/0037
USPC .......................................... 257/676; 438/674
See application file for complete search history.

(56) References Cited

U.S. PATENT DOCUMENTS

| | | | | |
|---|---|---|---|---|
| 2002/0055764 | A1* | 5/2002 | Malonek | A61N 1/05 607/122 |
| 2002/0145171 | A1* | 10/2002 | Miyachi | G02B 6/125 257/440 |
| 2003/0157244 | A1* | 8/2003 | Kawase | H01L 51/0004 427/58 |
| 2004/0210289 | A1* | 10/2004 | Wang | A61K 9/5094 607/116 |
| 2005/0027338 | A1* | 2/2005 | Hill | A61N 1/05 607/116 |
| 2007/0087564 | A1 | 4/2007 | Speakman | |
| 2009/0299167 | A1* | 12/2009 | Seymour | A61B 5/04001 600/393 |
| 2009/0316060 | A1* | 12/2009 | Nirmal | G02F 1/13439 349/35 |
| 2012/0048828 | A1* | 3/2012 | Kim | G06F 3/044 216/13 |
| 2012/0074394 | A1* | 3/2012 | Facchetti | C07C 43/20 257/40 |
| 2012/0248451 | A1* | 10/2012 | Sone | H01L 29/4908 257/59 |
| 2013/0146860 | A1* | 6/2013 | Toyama | H01L 51/0097 257/40 |
| 2014/0041904 | A1* | 2/2014 | Pedder | G06F 3/044 174/251 |
| 2014/0113129 | A1 | 4/2014 | Asal et al. | |
| 2014/0330355 | A1* | 11/2014 | Stevenson | A61N 1/08 607/116 |

FOREIGN PATENT DOCUMENTS

| | | |
|---|---|---|
| JP | 2008-258480 | 10/2008 |
| WO | 0143870 | 6/2001 |
| WO | 2006105478 | 10/2006 |
| WO | 2011112742 | 9/2011 |

OTHER PUBLICATIONS

Restriction Requirement for U.S. Appl. No. 14/056,450 mailed Jan. 23, 2015 (6 pages).

Cho, Young-Sang et al., "Colloidal Indium Tin Oxide Nanoparticles for Transparent and Conductive Films," Thin Solid Films, 515, pp. 1864-1871 (2006).

Tehrani, Payman et al., "Patterning Polythiophene Films Using Electrochemical Over-Oxidation," Technical Note, Institute of Physics Publishing, Smart Materials and Structures, 14, pp. N21-N25 (2005).

Final Office Action for U.S. Appl. No. 14/056,450 mailed Oct. 28, 2015 (8 pages).

* cited by examiner

MULTI-LAYERED STRUCTURE AND METHOD

BACKGROUND

One aspect relates to a layered structure and another to a method for producing a layered structure. Prior methods describe layered structures having layers differing in conductivity which are usually produced through the use of laborious sputtering processes. This involves the use of complex equipment for maintenance of the process conditions and, in addition, expensive methods for vaporization of the materials used for sputtering. In general, it is desired to overcome, at least in part, the disadvantages resulting according to the prior art.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
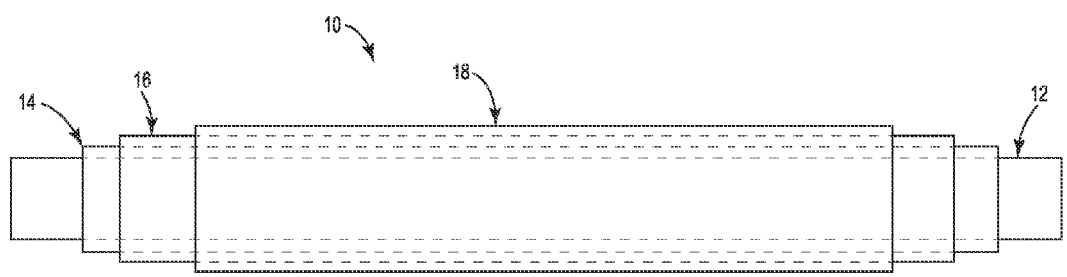
FIG. 1 illustrates a side view of a layered structure according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment provides an inexpensive and efficient method for producing a layered structure of at least three layers.

One embodiment provides a method for producing a layered structure of at least three layers that can be used to produce layers that are as thin as possible.

One embodiment provides a simple and rapid method for producing a layered structure of at least three layers of which at least two layers differ in conductivity, that is, of which at least one layer is electrically conductive and at least one second layer is insulating.

One embodiment provides a layered structure of at least three layers that is simple and inexpensive to produce.

One embodiment provides a measuring device having a layered structure, whereby the layered structure is at least as accurate, reliable or long-lasting in use as the measuring devices with layered structures known according to the prior art.

In one embodiment, "electrically conductive" means that the object referred to as being electrically conductive has a specific sheet resistance of less than 10 k$\Omega$ (10,000 Ohm), in one embodiment less than 5 k$\Omega$ or in one embodiment less than 1 k$\Omega$. In many cases, the specific sheet resistance is concurrently more than 1$\Omega$, in one embodiment more than 5$\Omega$, though. If the substrate includes multiple electrically conductive layers, the specific sheet resistance of each of said layers meets at least one of the preceding criteria. Several of the multiple electrically conductive layers can have the same or different sheet resistance values within the range of the criteria specified above.

In one embodiment, "insulating" or "insulative" mean that the object referred to as being insulating has a specific sheet resistance of more than 50 k$\Omega$, in one embodiment more than 500 k$\Omega$ or in one embodiment more than 1 M$\Omega$ (1,000,000 Ohm). In many cases, the specific sheet resistance is concurrently less than 100 M$\Omega$, in one embodiment less than 10 M$\Omega$, though. If the substrate includes multiple electrically conductive layers, the specific sheet resistance of each of said layers meets at least one of the preceding criteria. Several of the multiple electrically conductive layers can have the same or different sheet resistance values within the range of the criteria specified above.

In one embodiment, "biocompatible" means that the object referred to as being biocompatible meets the pertinent biocompatibility requirements according to the ISO 10993 1-20 standard.

According to one embodiment, a method for producing a layered structure includes providing a substrate;
 forming a first layer onto at least part of the substrate, the first layer being a first polymer;
 forming a second layer onto at least part of the first layer, the second layer being a second polymer;

wherein the substrate and the second layer are electrically conductive and the first layer is insulating or the substrate and the second layer are insulating and the first layer is electrically conductive; and characterized in that forming each of the first and second layers comprises forming such that each of the first and second layers is no more than one tenth of the thickness of the substrate.

In one embodiment, at least one of the first and second layers includes an electrically conductive PEDOT material. In one embodiment, forming each of the first and second layers includes forming such that each of the first and second layers is no more than one fiftieth of the thickness of the substrate. In one embodiment, forming of at least one of the first and second layers comprises masking ends of the layer to define contact areas that are configured for attaching an electrically conducting contact. In one embodiment, forming of at least one of the first and second layers includes using a conductive PEDOT polymer followed by using a chemical etch to change at least portions of the layer from conductive to insulative. In one embodiment, the method includes forming a third layer over the second layer, the third layer comprising an insulative photoresist material.

In the embodiments, the conductive polymers provide conductivity in a layer that is very thin, provides great flexibly and elongation, and that is easy to manufacture at relatively low cost. Furthermore, the embodiments significantly maintain the base shape, size, appearance and configuration of the substrate.

In one embodiment, a layered structure includes a substrate, a first layer over the substrate, and a second layer over the first layer. The substrate and the second layer are an electrically conductive material and the first layer is an insulating material or the substrate and the second layer are insulating material and the first layer is electrically conductive material, and that at least one of the first and second layers comprises an electrically conductive polymer. In one embodiment, at least one of the first and second layers comprises electrically conductive PEDOT. In one embodiment, each of the first and second layers are one tenth of the thickness of the substrate. In one embodiment, the layered structure has a length defining first and second ends and wherein at least one of the first and second layers extends substantially the length of the layered structure and includes contact areas proximate to the first and second ends that are configured for attaching an electrically conducting contact. In one embodiment the thickness of at least one of the first and second layers is in a range from 0.05 μm to 10 μm. In one embodiment, the substrate comprises one of a metal wire and metal insertion needle and at least one of the first and second layers is electrically conductive PEDOT. In one embodiment, the substrate and the first and second layers are biocompatible such that the layered structure is configured for implantation into the human body. In one embodiment, the substrate has a sheet resistance of less than 10 kΩ.

In the embodiments, the conductive polymers provide conductivity in a layer that is very thin, provides great flexibly and elongation, and that is easy to manufacture at relatively low cost. Furthermore, the embodiments significantly maintain the base shape, size, appearance and configuration of the substrate.

In one embodiment, a layered structure includes a conductive substrate, a first layer over the substrate, wherein the first layer comprises an insulating material and includes at least one access area, and a contact area at least partially within the access area and in conductive contact with the substrate. The first layer has a thickness that is no more than one tenth of the thickness of the substrate. In one embodiment, the contact area is an electrically conductive PEDOT material. In one embodiment, the access area is a hole in the first layer having a diameter of less than 0.4 mm. In one embodiment, each of the first layer and the contact area are no more than one tenth the thickness of the substrate. In one embodiment, the substrate, the contact area and the contact area are biocompatible such that layered structure is configured for implantation into the human body. In one embodiment, the thickness of the first layer is no more than one fiftieth of the thickness of the substrate.

The described embodiments can achieve very small contact areas within the first layer, which is itself very thin. This provides great flexibly and elongation, and is easy to manufacture at relatively low cost. Furthermore, the embodiments significantly maintain the base shape, size, appearance and configuration of the substrate.

FIG. 1 illustrates a layered structure 10 in accordance with one embodiment. In one embodiment, layered structure 10 includes substrate 12, first layer 14, second layer 16 and third layer 18. In one embodiment, substrate 12 is conductive metal medical component, such as a wire, which is also biocompatible. First layer 14 is insulating layer such as an insulative polymer, which is also biocompatible, that is formed over substrate 12. Second layer 16 is a conductive layer, such as a conductive polymer, which is also biocompatible, that is formed over first layer 14. Finally, third layer 18 is an insulating layer, such as an insulative polymer, which is also biocompatible, that is formed over second layer 16.

As such, in one embodiment layered structure 10 is a fully biocompatible medical device that is useful for implantation or insertion in the human body. Furthermore, with its alternating conductive and non-conductive layers, it is useful in many applications where multiple independent conductors are needed in a small package that does not significantly alter the base component, such as substrate 12. In this way, layered structure 10 provides functional capability in multiple layers, yet layered structure 10 significantly maintains the base shape, size, appearance and configuration of substrate 12.

Figure 2A:
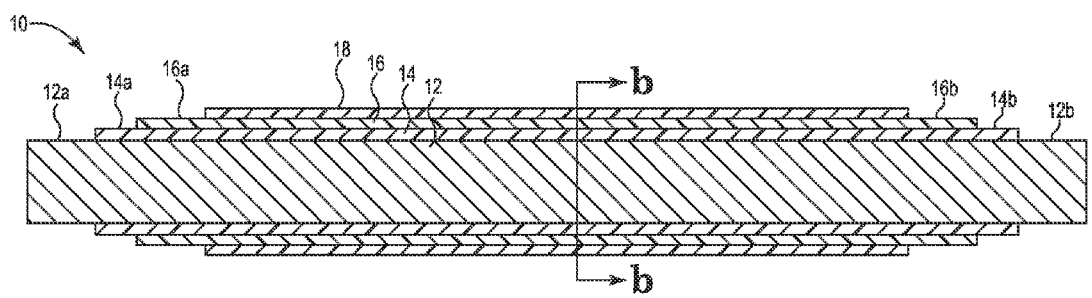
FIGS. 2a-2c illustrate respective length-wise and width-wise cross-sectional views of a layered structure according to various embodiments.
Figure 2B:
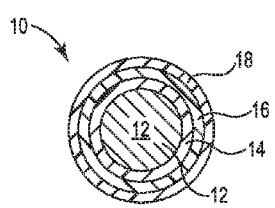

FIG. 2a illustrates a sectional view of layered structure 10 taken along its length, in accordance with one embodiment. FIG. 2b illustrates a sectional view of layered structure 10 from the line b-b in FIG. 2a. Layered structure 10 includes substrate 12, first layer 14, second layer 16 and third layer 18. As is apparent in the sectional view of FIG. 2a, in one embodiment, the ends of each of substrate 12 and layers 14, 16, and 18 are slightly staggered relative to each other. As such, substrate 12 includes exposed first and second contact areas 12a and 12b, which extend laterally beyond first layer 14 at opposite ends of layered structure 10. Similarly, second layer 16 includes exposed third and fourth contact areas 16a and 16b, which extend laterally beyond third layer 18 at opposite ends of layered structure 10.

First and second insulating areas 14a and 14b respectively insulate the area between first and third contact areas 12a and 16a and the area between second and fourth contact areas 12b and 16b. In one embodiment, sensors, measuring devices, wires or other conductive contacts can be attached to contact areas 12a, 12b, 16a and 16b as will be further discussed below. First and third layers 14 and 18 isolate conductive substrate 12 and conductive second layer 16 so that independent signals can be carried via layered structure 10 from first contact area 12a at one end to second contact are 12b at the other end (via substrate 12) and from third contact area 16a at one end to fourth contact are 16b at the other end (via second layer 16). Because layers 14, 16, and 18 are very thin and flexible, layered structure 10 significantly maintains the base shape, size, appearance and configuration of substrate 12.

Figure 2C:
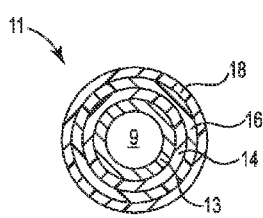

In one embodiment, substrate 12 of layered structure 10 illustrated in FIGS. 2a and 2b is a solid wire, such as a medical guide wire or the like that can be implanted or temporality inserted into a human body. In the embodiment illustrated in FIG. 2c, layered structure 11 includes a substrate 13 that is a wire with a lumen 9 running through its center. Layers 14, 16, and 18 are added as described above with respect to layered structure 10. As such, layered structure 11 can also be used in medical implant situations, and further provides the ability to transmit material, such as medicine or a bodily fluid, via lumen 9.

Figure 3A:
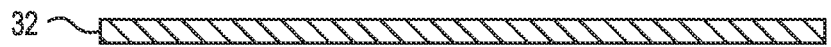
FIGS. 3a-3f are cross-sectional views illustrating a method of forming a layered structure according to one embodiment.
Figure 3B:
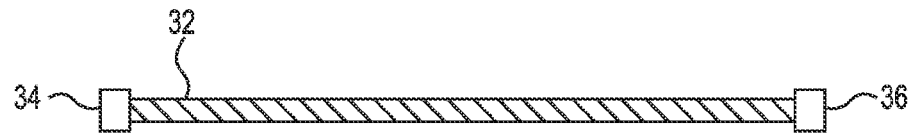

FIGS. 3a-3f illustrate sectional views of a method of forming a layered structure 50 (FIG. 3f) in accordance with one embodiment. A substrate 32 is illustrated in FIG. 3a. Substrate 32 is biocompatible and conductive, such as a medical wire. In FIG. 3b, first and second mask ends 34 and 36 are placed over substrate 32 at each of its respective ends. Masks 34 and 36 can be in a variety of forms, such as tape masks or a heat-shrink tube. In one embodiment, a polyimide tape is used for masks 34 and 36.

Figure 3C:

With masks 34 and 36 in place over substrate 32, first layer 38 is formed, as illustrated in FIG. 3c. In one embodiment, first layer 38 is a parylene coating that is a conductive insulator providing conductive isolation to substrate 32, except where first and second mask ends 34 and 36 prevented the formation of first layer 38. In one example, the parylene coating of first layer 38 is applied to substrate 32 at about 25 degrees C. under a pressure of about 0.1-1.0 Torr.

Figure 3D:
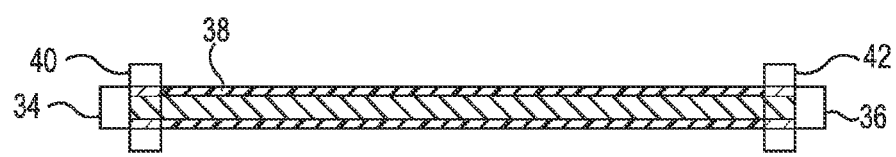
Figure 3E:
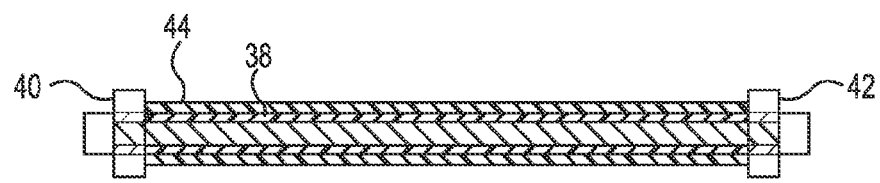

Next, third and fourth masks 40 and 42 are placed over the ends of first layer 38 immediately adjacent first and second masks 34 and 36, respectively, as illustrated in FIG. 3d. Masks 40 and 42 can also be in a variety of forms, such as tape masks, for example a polyimide tape, or a heat-shrink tube. With masks 40 and 42 in place, a second layer 44 is formed over first layer 38 between masks 40 and 42 as illustrated in FIG. 3e. In one embodiment, second layer 44 is a conductive layer, such as a conductive polymer.

In one embodiment, second layer 44 is a conductive polymer Poly(3,4-ethylenedioxythiophene)poly(styrenesulfonate), or PEDOT:PSS (hereinafter referred to as "PEDOT"), such as for example, a conductive polymer sold under the trade name CLEVIOS™. Second layer 44 may be applied in a variety of ways, for example, with deposition by in-situ polymerization, by printing or screen-printing, by spin coating, or by other known methods of application. In other embodiments, conductive polymers such as carbon nanotube conductive polymers or other conductive polymers can be used. In each case, the conductive polymers provide conductivity in a layer that is very thin, provides great flexibly and elongation, and that is easy to manufacture at relatively low cost.

Figure 3F:
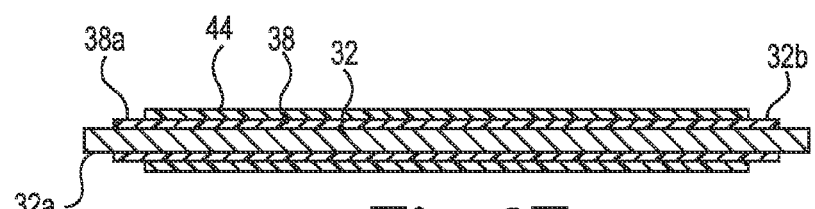

Once first and second masks 34 and 36 and third and fourth masks 40 and 42 are removed, layered structure 50 is formed as illustrated in FIG. 3f. As illustrated there, first and second contact areas 32a and 32b are located on the substrate 32 at the respective ends of layered structure 50, and will be accessible for attachment of sensors or other devices as described above with respect to layered structure 10. In addition, further layers can be readily added to layered structure 50 such that 2, 3, 4 or more contact areas with respective any added conductive layers are readily available for coupling sensors, measuring devices, wires or other conductive contacts useful in invasive or implantable medical devices.

In one embodiment of layered structure 50, substrate 32 is metal needle or wire having an outer diameter of about 0.5 mm. In other applications, substrate 32 may have a more rectangular shape, but have a thickness of about 0.5 mm. In some of the applications of such a needle, wire or similar device, it is important that independently accessible conductive contact areas are available on the needle or wire (such as contact areas 12a and 16a described above with respect to layered structure 10) for attaching sensor, measuring devices or the like. But, in some applications it is also important that the outer diameter or outer thickness of layered structure 50 does not significantly depart from the outer diameter or thickness substrate 32. Accordingly, in one embodiment, each of first layer 38, second layer 44, and any additional insulating and conductive layers added over them are orders of magnitude more thin than the outer diameter or thickness of substrate 32.

In one embodiment, each of first layer 38, second layer 44 and any additional insulating and conductive layers added over substrate 32 are no more than 50 microns, and in one embodiment each are between 2 and 10 microns. In such case, where substrate 32 is 0.5 mm in diameter or thickness and all subsequent added layers over it are no more than 50 microns, each added layer is no more than one tenth in thickness relative to the diameter or thickness of substrate 32. With each of these subsequent layers over substrate 32 having such relatively small thicknesses, the overall size of layered structure 50 does not significantly depart from that of substrate 32. This can be important in many medical applications where the size and shape of substrate 32, such as where it is an injection needle, must be kept limited in order for it to reach its targeted location without interfering or harming closely adjacent locations.

In addition, in one embodiment each of first layer 38, second layer 44, and any additional insulating and conductive layers over substrate 32 are each polymer layers. As such, unlike metallic coated layers, for example, each subsequent layer over substrate 32 is extremely flexible. This provides flexibility to layered structure 50 not available in prior devices. In one embodiment, each subsequent layer over substrate 32 is a polymer material that can sustain elongation of up to 300% without damaging the material, causing splits, or otherwise compromising the layers. By comparison, layers that are metallic-based and related coatings often fail after elongation on only 25%. Accordingly, layered structure 50 with polymer layers over substrate 32 is a flexible structure useful in many medical applications.

Furthermore, because layered structure 50 uses a conductive polymer coating like PEDOT and an insulative coating like parylene, both of which are biocompatible, it is readily useable as a device that is either inserted or implanted into a human body. Some metallic and other related coatings can react with blood and body fluids and partially dissolve components into the blood. Because the insulative and conductive coatings of layered structure 50 are biocompatible polymers, it will not be absorbed into the body.

In addition, because layered structure 50 uses a conductive polymer coating like PEDOT and an insulative coating like parylene, both of which can be kept extremely thin, yet at the same time not risk having pin holes, such as can be the case when metallic coatings are used in very thin layers. Such pin holes that occur with metallic coatings will cause subsequent layers to flow into the pin holes and jeopardize the integrity of the layers.

Figure 4A:
FIGS. 4a-4c are cross-sectional views illustrating a method of forming a layered structure according to one embodiment.
Figure 4B:
Figure 4C:
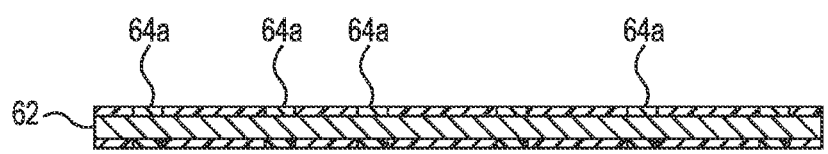

FIGS. 4a-4c illustrate sectional views of a method of forming a layered structure 70 in accordance with one embodiment. A substrate 62 is illustrated in FIG. 4a. Substrate 62 is biocompatible and conductive, such as a medical wire. In FIG. 4b, a first layer 64 is formed over substrate 62. In one embodiment, first layer 64 is a conductive layer, such as a PEDOT conductive polymer. For example, first layer 64 is a conductive polymer sold under the trade name CLEVIOS™. First layer 64 is conductive and may be applied in a variety of ways, for example, with deposition by in-situ polymerization, by screen-printing, or by other known methods of application.

Once first layer 64 is applied it can be selectively treated with CLEVIOS™ Etch, which destroys the conductivity of the CLEVIOS™ conductive polymer in the areas where the CLEVIOS™ Etch is applied. FIG. 4c illustrates isolating areas 64a where CLEVIOS™ Etch has been applied thereby rendering those areas 64a as non-conductive and also thereby defining areas of conductivity in first layer 64 between the isolating areas 64a. As such, layered structure 70 provides multiple conductive contact areas that are readily available for coupling sensors, measuring devices, wires or other conductive contacts useful in invasive or implantable medical devices.

Since CLEVIOS™ Etch can be readily applied by printing, the areas of conductivity and insulating properties can be precisely defined in a layer without need for masking. Avoiding masking allows for automation in manufacturing processes, which leads to significant cost savings in production. As with the previous process, more layers can be added to create unique multilayer devices with various configurations of conductivity and insulating properties between layers and even within a single layer of the device.

Figure 5A:
FIGS. 5a-5d are cross-sectional views illustrating a method of forming a layered structure according to one embodiment.
Figure 5B:

FIGS. 5a-5d illustrate sectional views of a method of forming a layered structure 90 in accordance with one embodiment. A substrate 82 is illustrated in FIG. 5a. Substrate 82 is biocompatible and conductive, such as a medical wire. In FIG. 5b, first layer 84 is formed over substrate 82. In one embodiment, first layer 84 is a Poly(methyl methacrylate) (PMMA) coating that is a conductive insulator providing conductive isolation to the substrate 82. In one example, the PMMA coating of first layer 84 is dip coated to cover substrate 82.

Figure 5C:
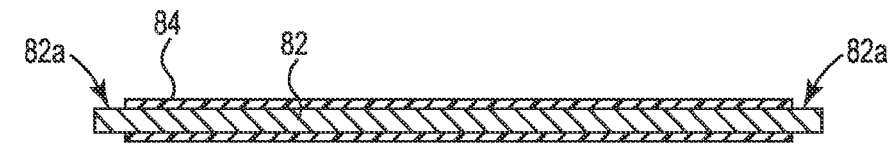
Figure 5D:
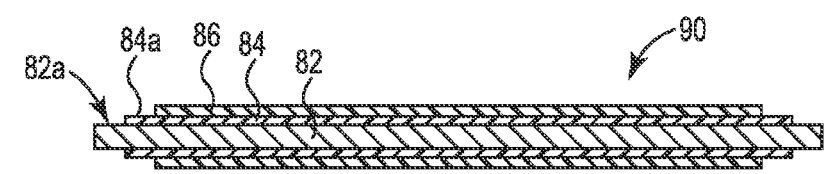

Next, first and second contact areas 82a and 82b are exposed on the substrate 82 by laser ablation of first layer 84 in those areas, as illustrated in FIG. 5c. In FIG. 5d, a second layer 86 is formed over first layer 84. In one embodiment, second layer 86 is a conductive polymer, such as PEDOT. In another embodiment, second layer 86 is a nano gold coating that is applied via inkjet printing. In such case, printing allows exact dimensions so that no masking is needed in forming layered structure 90. This allows for the use of automation in manufacturing, which leads to significant cost savings in production.

As illustrated in FIG. 5d, first and second contact areas 82a and 82b are located on the substrate 82 at the respective ends of layered structure 90, and will be accessible for attachment of sensors or other devices as described above with respect to layered structure 10. In addition, further layers can be readily added to layered structure 90 such that 2, 3, 4 or more contact areas with respective conductive layers are readily available for coupling sensors, measuring devices, wires or other conductive contacts useful in invasive or implantable medical devices.

Figure 6A:
FIGS. 6a-6d are cross-sectional views illustrating a method of forming a layered structure according to one embodiment.
Figure 6B:
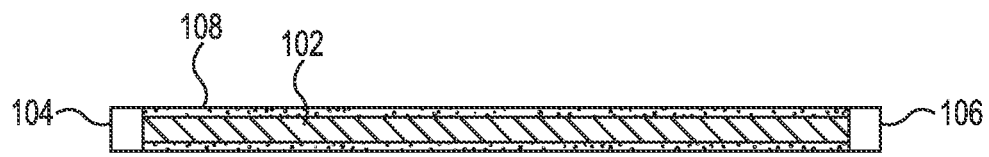

FIGS. 6a-6d illustrate sectional views of a method of forming a layered structure 120 (FIG. 6d) in accordance with one embodiment. A substrate 102 is illustrated in FIG. 6a. Substrate 102 is biocompatible and conductive, such as a medical wire. In FIG. 6b, first and second mask ends 104 and 106 are placed over substrate 102 at each of its respective ends. Masks 104 and 106 can be in a variety of forms, such as photomasks or other masks typically used in photolithography processes.

Figure 6C:
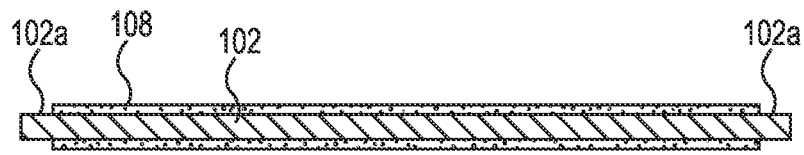

With masks 104 and 106 in place over substrate 102, first layer 108 is formed, as illustrated in FIG. 6b. In one embodiment, first layer 108 is a photoresist layer that is sputtered onto substrate 102, or otherwise applied. In one embodiment, first layer 108 is SU-8 photoresist, and is accordingly biocompatible and insulative. In FIG. 6c, first layer 108 is exposed to a UV source or laser such that the portion on first layer 108 left behind provides an insulating layer over substrate 102, except at the contact areas 102a, where masks 104 and 106 were located and then removed. In addition, a photomask can be used in conjunction with a photoresist layer as first layer 108, in order to selectively coat substrate 102. For example, a photomask can be used so that only sections of first layer 108 will be insulative, such as the layer illustrated in FIG. 4c. Then, conductive material can be formed in between these insulative sections, also as illustrated in FIG. 4c.

Figure 6D:
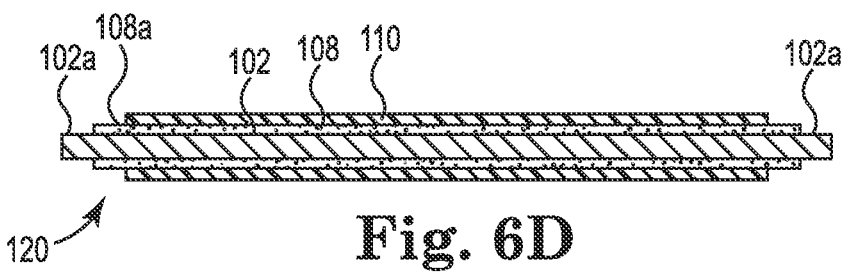

A second layer 110 is then formed over first layer 108 as illustrated in FIG. 6d to form layer structure 120. In one embodiment, second layer 110 is a conductive polymer, such as PEDOT. In another embodiment, second layer 110 is a nano gold coating that is applied via inkjet printing. In such case, printing allows exact dimensions so that no masking is needed in forming second layer 110. This allows for the use of automation in manufacturing, which leads to significant cost savings in production.

As with previous illustrations, first and second contact areas 102a and 102b are located on substrate 102 at the respective ends of layered structure 120, and will be accessible for attachment of sensors or other devices. In addition, just as all the embodiments above, further layers can be readily added to layered structure 120 such that 2, 3, 4 or more contact areas with respective conductive layers are readily available for coupling sensors, measuring devices, wires or other conductive contacts useful in invasive or implantable medical devices.

Figure 7:
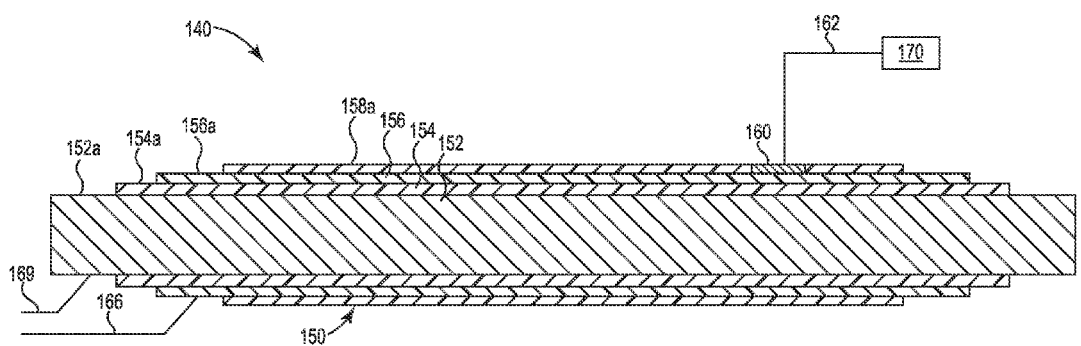
FIG. 7 illustrates an implantable medical system including a layered structure according to one embodiment.

For example, FIG. 7 illustrates an implantable medical system 140 including a layered structure 150 according to one embodiment. Layered structure 150 includes substrate 152, which is conductive, first layer 154, which is insulating, second layer 156, which is conductive, and third layer 158, which is insulating. As with the above embodiments, the ends of each of substrate 152 and layers 154, 156, and 158 are slightly staggered relative to each other thereby defining contact area 152a for substrate 152 and contact area 156a for second layer 156.

In one embodiment of medical device 140, wire sensors 164 and 166 are respectively coupled to contact areas 152a and 156a. These wire sensors 164 and 166 may be wires, coils or other conductive elements that can receive signals, such as signals within a human body. Signals from wire sensors 164 and 166 are then respectively transmitted along substrate 152 and second layer 156. In one embodiment, it may be advantageous for a signal to be monitored or otherwise received by an electronic device 170. In some embodiments, the end portion opposite contact areas 152a and 156a may not be convenient for attachment to such a device. Accordingly contact area 160 is formed in second layer 158, such that coupling 162 can couple signals from second layer 156, through third layer 158 to electronic device 170.

This configuration is readily created using the exemplary layers described in the above embodiments. For example, second layer 158 could initially be formed using the conductive polymer CLEVIOS™. Next, the CLEVIOS™ Etch can be applied to the entire second layer 158 with the exception of the contact area 160. In this way, a conductive path is established between second layer 156 and electronic device 170. In another example, second layer 158 could be formed from a photolithographic process where the entire second layer 158 with the exception of the contact area 160 is photoresist, and contact area 160 is filled in with a conductive material.

Figure 8A:
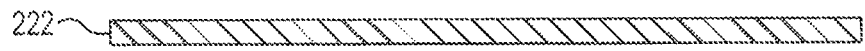
FIGS. 8a-8d are cross-sectional views illustrating a method of forming a layered structure according to one embodiment.
Figure 8B:

FIGS. 8a-8d illustrate sectional views of a method of forming a layered structure 250 (FIG. 8d) in accordance with one embodiment. A substrate 222 is illustrated in FIG. 8a. Substrate 222 is biocompatible and conductive, such as a medical wire. In FIG. 8b, first layer 224 is formed over substrate 222. In one embodiment, first layer 224 is a Poly(methyl methacrylate) (PMMA) coating that is a conductive insulator providing conductive isolation to the substrate 222. In one example, the PMMA coating of first layer 224 is dip coated to cover substrate 222.

Next, first, second and third access areas 226a, 226b and 226c are formed in first layer 224 such that substrate 222 is exposed through first layer 224 in those areas. In one embodiment, first access area 226a exposes just a small section of substrate 222 on a top surface and does not fully expose substrate 222 around its full circumference. In one embodiment, second access area 226b does fully expose substrate 222 around its full circumference. In other embodiments, additional or fewer access areas may be used to provide varying degrees of access to substrate 222. In one embodiment, first, second and third access areas 226a, 226b and 226c are formed by laser ablation of first layer 224 in those areas, although in other embodiments masking and other techniques as described above may be used.

Figure 8C:
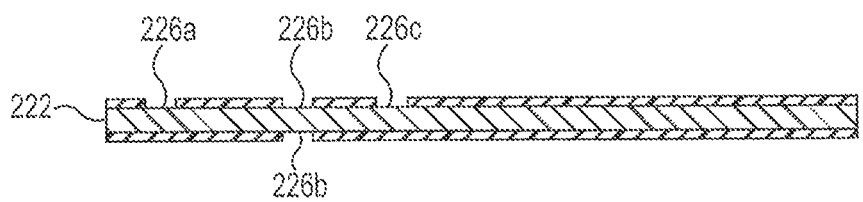
Figure 8D:
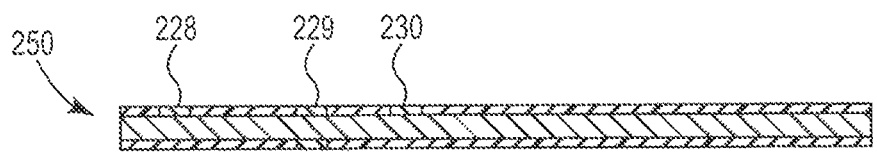

In FIG. 8d, first, second and third contact areas 228, 229 and 230 are formed within first, second and third access areas 226a, 226b and 226c and directly over substrate 222. In one embodiment, first, second and third contact areas 228, 229 and 230 are formed with a conductive polymer, such as PEDOT. Such conductive polymers can be applied by dip coating or other various techniques described above. In such embodiments, masking as described above can be used to tailor the dimensions of contact areas 228/229/230 quite tightly. In other embodiments, first, second and third contact areas 228, 229 and 230 are formed with a nano gold coating that is applied via inkjet printing. In such case, printing allows exact dimensions so that no masking is needed in forming layered structure 250. This allows for the use of automation in manufacturing, which leads to significant cost savings in production. In another embodiment, the configuration of layered structure 250 is achieved using CLEVIOS™ and CLEVIOS™ Etch with masking as discussed in the above embodiments.

The described embodiments of layered structure 250 can achieve very small contact areas 228/229/230 within first layer 224, which is itself very thin. For example, in one embodiment substrate 222 is a metal wire with a diameter of 0.5 mm and first layer 224 is an insulative polymer with a thickness of no more than 50 microns, and in one embodiment between 2 and 10 microns. In addition, contact areas 228/229/230 can achieve conductive contact with substrate 222 even with very small first, second and third access areas 226a, 226b and 226c. For example, first layer 224 can be laser ablated so that access areas 226a/226b/226c are just small diameter holes, in one embodiment having a diameter of less than 0.4 mm. In another embodiment, access areas 226a/226b/226c are more slit or rectangular shapes and have a width along substrate 222 that is 0.3 mm or less. Contact areas 228/229/230 can be formed exclusively within access areas 226a/226b/226c, or may even be formed to overlap first layer 224 slightly, but will still achieve conductive contact with substrate 222 as long as at least some portion of contact areas 228/229/230 are formed within access areas 226a/226b/226c.

As illustrated in FIG. 8d, contact areas 228/229/230 on layered structure 250, and can, for example, be located toward a distal end of layered structure 250. Signals can then be sent and/or received via substrate 222 at a proximal end of layered structure 250 to and from contact areas 228/229/230 at the distal end. In this way, when substrate 222 is a medical device configured for insertion into the human body, contact areas 228/229/230 can be advantageously used to measure signals within the body, deliver electrical stimulation to precise locations within the body or for similar uses of signals and electrical pulses, while access to these signals is provided at a location remote from where they are measured or delivered. Because both first layer 224 and contact areas 228/229/230 are very thin polymers, the overall size of layered structure 250 closes approximates substrate 222. Furthermore, the flexibility of these polymer materials ensures that layered structure 250 is no less flexible than is substrate 222.

In embodiments where contact areas 228/229/230 are dip coated within access areas 226a/226b/226c, the contact areas 228/229/230 can achieve very thin dimensions, yet at the same time provide a relatively consistent thickness across access areas 226a/226b/226c. This is not the case for sputter coating, which is common for applying thin metallic coatings. In such sputter coating processes, the device to be coated is placed in a chamber with essentially a cloud of atoms, such that everything in the chamber is coated with the conductive metallic material. In such environments, there is unevenness to the thickness of the applied layer due to the so-called "shadow effect." With such a shadow effect, areas adjacent to vertical sections, such as the walls on either side of access areas 226a/226b/226c seen in FIG. 8c, are blocked by the vertical walls and are covered less than areas away from the side walls, such as in the center of access areas 226a/226b/226c. This unevenness of coverage caused by the shadow effect can cause problems with the integrity of the applied layer. This is not the case of the substantially even thickness layers of the dip-coated conductive layers.

For each of the layered structures illustrated in the above embodiments, the substrate is conductive. It is also possible in each case that the substrate is insulative. Generally, when the substrate is conductive, the first layer is then insulative, the second layer conductive and continuing alternating thereafter. When the substrate is insulative, the first layer is then conductive, the second layer insulative and continuing alternating thereafter. In each case, the substrate is generally a thicker layer that is useful in a medical device application, with each subsequent layer being an order of magnitude thinner than the substrate to essentially conform to the dimensions of the substrate.

It is also to be understood that the features of the various exemplary embodiments described above may be combined with each other, unless specifically noted otherwise. For example, masking techniques described in FIGS. 3a-3f could be used in forming some layers, while CLEVIOS™ Etch could be used in forming other layers, while laser ablation could be used in other layers, while photoresist techniques could be used in other layers, all in the same layered structure.

Figure 9:
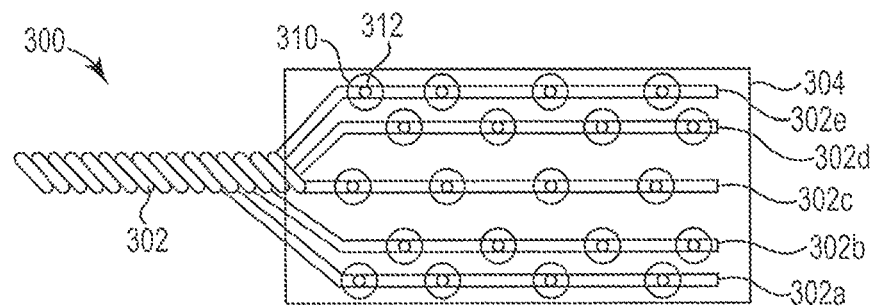
FIG. 9 illustrates an implantable medical system including a layered structure according to one embodiment.

FIG. 9 illustrates an implantable medical system 300 including a multifilar layered structure 302 and electrode paddle 304 according to one embodiment. Multifilar layered structure 302 includes first-fifth layered structures 302a-302e, each of which are layered structures as described above with respect to the various embodiments and combinations thereof, and each of which are twisted together to form multifilar 302. In one embodiment, fifth layered structure 302e, for example, includes a wire substrate covered with insulating layer. Furthermore, access areas 312 (only labeled in one instance for simplifying the figure) have been laser ablated into the insulating layer and contact areas 310 (also only labeled in one instance for simplifying the figure) have been formed at least partially within access areas 312 (such as with the process described with respect to FIGS. 8A-8D above). As such, each of contact areas 310 are electrically coupled to the wire substrate. Each of contact areas 310 are then oriented on a face of electrode paddle 304. Accordingly, the various contact areas 310 of electrode paddle 304 can be energized independently by selectively energizing one or more of first-fifth layered structures 302a-302e.

In one embodiment, implantable medical system 300 is completely biocompatible such that it can be partially or completely implanted in a human body. Electrode paddle 304 can be located adjacent tissue within the body that will receive electrical energy via one or more contact areas 310. Electrical pulses can then be delivered to various locations on the tissue depending on which layered structures 302a-302e, and accordingly, which contact areas 310, are energized. Because contact areas 310 are distributed about electrode paddle 304 such that they are spaced apart from each other, certain areas of tissue or the like can be targeted by selectively energizing layered structures 302a-302e.

Figure 10A:
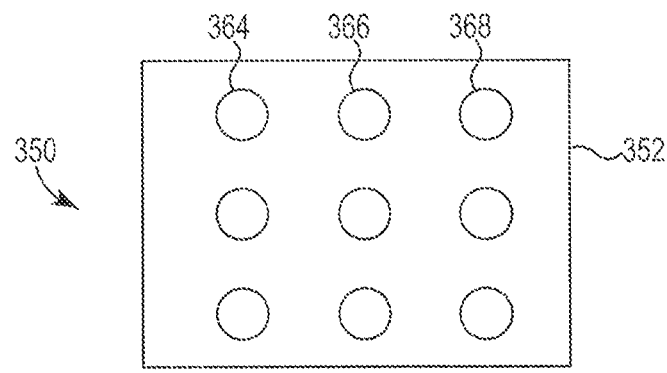
FIGS. 10a and 10b illustrate top and sides views of an implantable medical system including a layered structure according to one embodiment.
Figure 10B:
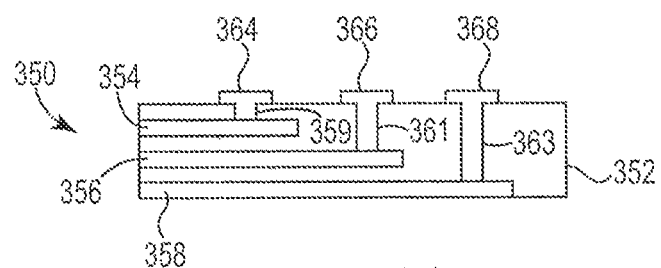

Similarly, FIGS. 10a and 10b illustrate an implantable medical system 350 including a multilayered structure 352 according to one embodiment. In one embodiment, multilayered structure 352 has a face with contact areas 364/366/368 (and other contact areas are illustrated without labels to simplify the figure). Each contact area is electrically coupled to one conductive layer 354/356/358. For example, first conductive layer 354 is coupled to first contact area 364, second conductive layer 356 is coupled to second contact area 366, and third conductive layer 358 is coupled to third contact area 368. Additional contact areas and corresponding conductive layers can be added as desired.

In each case, respective conductive layers 354/356/358 are electrically coupled to contact areas 364/366/368 with contact vias 359/361/363. The remaining portions of multilayered structure 352 are insulative so that each electrical signal on first conductive layer 354 is coupled only to first contact area 364, each electrical signal on second conductive layer 356 is coupled only to second contact area 366, and electrical signal on third conductive layer 358 is coupled only to third contact area 368. Each of conductive layers 354/356/358 and contact areas 364/366/368 can be constructed as described above with respect to FIGS. 8A-8D or any of the other various embodiments, and combinations thereof.

In one embodiment, implantable medical system 350 is completely biocompatible such that it can be partially or completely implanted in a human body. Just as with electrode paddle 304 above, the face of multilayered structure 352 can be located adjacent tissue within the body that will receive electrical energy via contact areas 364/366/368. Electrical pulses can then be delivered to various locations on the tissue depending on which conductive layers 354/356/358, and accordingly, which contact areas 364/366/368, are energized.

Many such useful medical systems can be constructed using the layer structures according to various embodiments herein. Although the above examples discuss a substrate that is generally cylindrical, such as a wire or a needle, other configurations are also possible. A substrate can have any geometrical shape that is known to, and deemed to be suitable for use in various medical applications. For example, a planar or arced surface such as, for example, a planar or arced plate, a planar or arced disc or a straight or curved tube may be used. In one embodiment, the substrate is coated according to the specified method on at least one surface of the substrate or on multiple surfaces, or on all surfaces, of the substrate. Different surfaces of the substrate can be provided with different or identical layered structures. In one embodiment, all surfaces of the substrate are simultaneously subjected to the method according to one embodiment in a single step. In this case, all surfaces treated according to the method have the same layered structure. The method according to one embodiment is carried out in discontinuous manner as an immersion procedure. The method according to one embodiment can just as well be carried out continuously as a continuous system.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method for producing a layered structure comprising:
   providing a substrate having a thickness and comprising a material that is biocompatible;
   forming a first layer onto at least part of the substrate, the first layer being a first biocompatible polymer;
   forming a second layer onto at least part of the first layer, the second layer being a second biocompatible polymer;
   wherein the substrate and the second layer are electrically conductive and the first layer is insulating or the substrate and the second layer are insulating and the first layer is electrically conductive; and
   characterized in that forming each of the first and second layers comprises forming such that each of the first and second layers is no more than one tenth of the thickness of the substrate and such that each are configured for implantation within the human body.

2. The method according to claim 1, wherein at least one of the first and second layers comprises an electrically conductive PEDOT material.

3. The method according to claim 1 characterized in that forming each of the first and second layers comprises forming such that each of the first and second layers is no more than one fiftieth of the thickness of the substrate.

4. The method according to claim 1, wherein forming of at least one of the first and second layers comprises masking ends of the layer to define contact areas that are configured for attaching an electrically conducting contact.

5. The method according to claim 1, wherein forming of at least one of the first and second layers comprises using a conductive PEDOT polymer followed by using a chemical etch to change at least portions of the layer from conductive to insulative.

6. The method according to claim 1, further comprising forming a third layer over the second layer, the third layer comprising an insulative photoresist material.

7. A method for producing a layered cylindrical structure comprising:
   providing a substrate having a diameter and comprising a material that is biocompatible;
   forming a first layer onto at least part of the substrate, the first layer being a first biocompatible polymer;
   forming a second layer onto at least part of the first layer, the second layer being a second biocompatible polymer, such that both the first and second layers are configured for implantation within the human body;
   wherein the substrate and the second layer are electrically conductive and the first layer is insulating or the substrate and the second layer are insulating and the first layer is electrically conductive; and
   characterized in that forming each of the first and second layers comprises forming such that each of the first and second layers has a thickness that is no more than one tenth of the diameter of the substrate such that overall dimensions of the layered structure are substantially determined by the diameter of the substrate.

8. The method of claim 7, wherein providing the substrate comprises providing one of a wire and a needle.

9. The method according to claim 7, wherein at least one of the first and second layers comprises an electrically conductive PEDOT material.

10. The method according to claim 7 characterized in that forming each of the first and second layers comprises forming such that each of the first and second layers is no more than one fiftieth of the thickness of the substrate.

11. The method according to claim 7, wherein forming of at least one of the first and second layers comprises masking ends of the layer to define contact areas that are configured for attaching an electrically conducting contact.

12. The method according to claim 7, wherein forming of at least one of the first and second layers comprises using a conductive PEDOT polymer followed by using a chemical etch to change at least portions of the layer from conductive to insulative.

13. The method according to claim 7, further comprising forming a third layer over the second layer, the third layer comprising an insulative photoresist material.

* * * * *